(12) United States Patent
Crunkleton

(10) Patent No.: US 6,881,196 B2
(45) Date of Patent: Apr. 19, 2005

(54) SYMPTOMATIC RELIEF FOR SOFT CORNS

(76) Inventor: James A. Crunkleton, 66 Tinsley Way, Senoia, GA (US) 30276

( * ) Notice: Subject to any disclaimer, the term of this patent is extended or adjusted under 35 U.S.C. 154(b) by 210 days.

(21) Appl. No.: 10/370,244

(22) Filed: Feb. 20, 2003

(65) Prior Publication Data

US 2004/0167454 A1 Aug. 26, 2004

(51) Int. Cl.$^7$ .................................................. A61F 5/00
(52) U.S. Cl. ................................ 602/5; 602/30; 36/94; 36/95; 128/893; 128/894; 128/898; 264/222; 264/223
(58) Field of Search .............................. 602/5, 30, 31, 602/43, 58; 128/893, 894, 898, 845, 882; 264/219, 220, 221, 222, 223, 224, 225, 226, 227; 601/27; 36/94, 95

(56) References Cited

U.S. PATENT DOCUMENTS

| | | | | |
|---|---|---|---|---|
| 1,026,786 A | * | 5/1912 | Brandenburg | 128/893 |
| 1,054,934 A | * | 3/1913 | Packard | 128/893 |
| 1,690,395 A | * | 11/1928 | Biren | 128/893 |
| 2,115,237 A | * | 4/1938 | Scholl | 128/893 |
| 2,464,457 A | * | 3/1949 | Madaio | 128/893 |
| 2,646,795 A | | 7/1953 | Scholl | |
| 2,943,623 A | * | 7/1960 | Thompson | 128/893 |
| 2,949,112 A | | 8/1960 | Murray | |
| 3,063,555 A | * | 11/1962 | Hanington | 128/894 |
| 3,088,461 A | * | 5/1963 | Levitt | 128/894 |
| 3,253,591 A | * | 5/1966 | Scholl | 128/894 |
| 3,482,569 A | * | 12/1969 | Raffaelli, Sr. | 128/894 |
| 3,487,832 A | * | 1/1970 | Spence | 128/894 |
| 4,877,018 A | | 10/1989 | Ikebe | |
| 5,453,083 A | | 9/1995 | Kasahara | |
| 5,497,789 A | | 3/1996 | Zook | |
| 6,238,357 B1 | | 5/2001 | Kawaguchi | |
| 6,303,140 B1 | | 10/2001 | Dever | |

* cited by examiner

*Primary Examiner*—Fadi H. Dahbour
(74) *Attorney, Agent, or Firm*—Technoprop Colton LLC

(57) ABSTRACT

A system, method and device for the symptomatic relief for soft corns by injecting a medical grade molding substance between the toes between which a corn is located, forming a molded-in-place, custom-shaped high definition mold, unique to the individual's physical conformation and which reduces friction and eliminates pressure points on the corn.

37 Claims, 4 Drawing Sheets

SYMPTOMATIC RELIEF FOR SOFT CORNS

BACKGROUND OF THE INVENTION

1. Technical Field

The present invention relates generally to the field of pain relief for soft corns, and more specifically to a method and device for the symptomatic relief for soft corns on the feet, the device having the ability to conform to the shape of the corn in a manner that more evenly distributes pressure throughout the device, thus alleviating pressure on the corn and reducing pain.

2. Prior Art

Many and various types of corn cushions and pads have been developed for relieving the pain associated with soft corns. Historically, pads for corns have been manufactured from compressible materials such as felt or foamed latex. This trend continues today as evidenced by the large number of such products available on the over-the-counter foot care market. These products are typically doughnut-shaped and are placed around the corn. However, many people still have significant pain from the corn even when using these products.

U.S. Pat. No. 2,646,795 to Scholl discloses a corn cushion or pad that is applied to the top of the toe and over a joint of a toe so to wholly enclose the corn and reduce the pressure on the toe. U.S. Pat. No. 2,949,112 to Murray discloses a toe positioner for maintaining greater accuracy and control of toes during the making of casts or the making of shoes. U.S. Pat. No. 4,877,018 to Ikebe et al. discloses a device for deodorizing and drying portions between toes that comprises two rod-shaped flexible fibrous elements or layers formed of a large number of fibers that are positioned between toes.

U.S. Pat. No. 5,453,083 to Kasahara discloses a valgus big toe rectifying supporter that can help prevent pain in and around a valgus big toe and its nail by using a securing band and a resilient member (such as a sponge) and as applied, the securing band and the resilient member secure the big toe in place. U.S. Pat. No. 5,497,789 to Zook discloses a padding and medicating device for corns, hammertoes, bunions, blisters and the like comprising a non-compressible or viscoelastic gel that is directly impregnated on a carrier structure of elastic fiber. In the Zook '789 device, the viscoelastic gel conforms to the shape of the lesion in a manner that dissipates externally applied pressure throughout the fabric-gel-tissue system, and the gel is retained on and compressed against the body part being treated by the elastic tension of the fabric.

U.S. Pat. No. 6,238,357 to Kawaguchi discloses a health appliance comprising an inflatable member that fits between toes (or fingers) that expands so as to widen the space between toes (or fingers). U.S. Pat. No. 6,303,140 to Dever et al. discloses a plaster preparation comprising and releasing an active ingredient for the treatment of corns, callus, and warts. The Dever '140 preparation comprises synthetic rubber, a reinforcing agent (such as silica), a tackifier, and a pharmaceutically acceptable salt, and discloses a drug carrier for efficaciously and controllably applying a drug to the surface of a corn, callus, or wart.

While the prior art proceeds to disclose an array of corn cushions and pads for relieving the pain associated with soft corns, each of these devices is not a custom-shaped and sized device. What is needed but not found in the prior art is a method and device for the symptomatic relief of soft corns that significantly eliminates the pressure points that still remain with other solutions. Previous inventions attempt to address the problem, not the underlying cause of corns, which is the elimination of localized pressure points. Other remedies offer some degree of relief by increasing the area of the pressure point associated with the formation of soft corns in minimal portions. The result being that these remedies have the effect of making the corn larger than its original size by increasing the area of pressure in one selected area.

It is to these needs and others that the present invention is directed. By utilizing a mold-in-place process, a greater surface area of the toe shares the pressure of the corn equally, thus substantially eliminating a selected pressure point. In addition, further advantages of the present invention are that the device properly adheres to the toe, even when the corn is on a joint of the toe, and does not irritate healthy tissue surrounding the corn and the adjacent toes.

BRIEF SUMMARY OF THE INVENTION

The present invention generally described is a method and device for the relief of pain caused by soft corns on the feet, generally on or between the toes. More specifically, the invention is an entire system, including a method and device for the symptomatic relief of pain caused by soft corns. Briefly, the invention comprises a molded-in-place device that conforms to the shape of the corn, thus reducing friction and eliminating pressure points on the corn by increasing the putative surface area of the corn.

One embodiment of the invention comprises a spacer, a mold dam, and a mold applicator containing a mold material. The spacer is inserted between the tips of the adjoining affected toes, that is, the toes having a corn therebetween. When inserted between the tips of toes, the spacer slightly separates the toes and leaves a small space preferably no more than about the thickness of a dime between the closest point between the toes. More specifically, the spacer slightly separates the corn on one toe from touching the adjacent toe.

With the spacer in place, the mold dam is applied to the bottom of the toes and foot. In one embodiment, the mold dam is applied starting first at the ball of the foot and working towards the tips of the toes, stopping at the top of the spacer. The mold dam is a thin piece of material having a relatively light adhesive on one side that can releasably adhere to the user's foot. The mold dam acts as the floor to catch the mold material and is used to secure the mold material between the toes and ensure that the mold material remains in the proper position while curing.

With the spacer and dam in place, the tip of the mold applicator is inserted between the appropriate toes, preferably tilted toward the tips of the toes. The mold applicator comprises a mold material receptacle, an applicator tip and a dispensing mechanism, and is generally a double-barreled plunger-type applicator. The mold applicator is operated by dispensing the mold material to fill the gap between the appropriate toes. As the mold material is applied, the mold applicator is lifted upward and rearward with the top layer of mold material being applied with a forward motion towards the tips of the toes. The mold material can completely fill the space between the toes all the way to the tips of the toes. The mold material can be applied in an amount sufficient to fill the space between the toes to prevent, when cured, the corn from touching or being forced against the neighboring toe. Too much mold material should not be applied as this will force the toes apart farther than desired or necessary.

The mold material can be any soft, flexible and sculptable substance having the ability to conform to an object in fine detail, release little heat upon curing, and set easily without contracting as it cures. For example, the mold material can be any of the known or future developed one-, two- or multi-part materials that starts off soft, flexible and/or sculptable and cures to a soft, generally flexible material, yet is strong enough to maintain its shape. Once the mold material has set between the toes, the mold dam and spacer are removed. The toes can be gently pulled apart and away from the molded device. The molded device can be removed and trimmed of any external flashing using a sharp knife, razor blade or scissors. Care should be taken not to cut or trim the sides where the molded device comes in contact between the toes.

The completed molded device conforms to the shape of the corn in a manner that distributes pressure throughout the device, thus alleviating pressure on the corn and reducing pain. Further, because pressure is distributed more evenly and the device is custom fit to the user, the device does not irritate healthy tissue surrounding the corn and the adjacent toes. If, after a week or two of using the molded device, the corns start to go away, a new molded device can be made. This will prevent the occurrence of new pressure points resulting in the formation of new corns.

Therefore a first feature of the present invention is to provide a method and device for the symptomatic relief for soft corns. It is a second feature of the device to redistribute the pressure on the corn throughout the device and the surrounding healthy tissue, thus alleviating pressure on the corn and reducing pain. The device does not irritate healthy tissue surrounding the corn and the adjacent toes and can be reused until the corn is gone or removed surgically. Further, the device properly adheres to the toe, even when the corn is on a joint of the toe, without reliance upon an article of footwear or an attaching band or device. It is another feature of the present invention to provide a method for the symptomatic relief for soft corns that is quick and easy to use.

These features, and other features and advantages of the present invention will become more apparent to those of ordinary skill in the art when the following detailed description of the preferred embodiments is read in conjunction with the appended figures.

DETAILED DESCRIPTION OF THE PREFERRED EMBODIMENTS

The present invention relates generally to the field of pain relief for soft corns, and more specifically to a method and device for the symptomatic relief of the pain caused by soft corns. The device of the present invention intimately encases the corn so as to transfer all or a significant amount of the pressure away from the corn to surrounding healthy tissue and at the same time prevents irritation of that tissue. The present invention uses common dental molding medium or a similar material to buffer the corn and uses a dam under the toes to make sure the dental molding medium remains in the proper position while curing.

Figure 1:
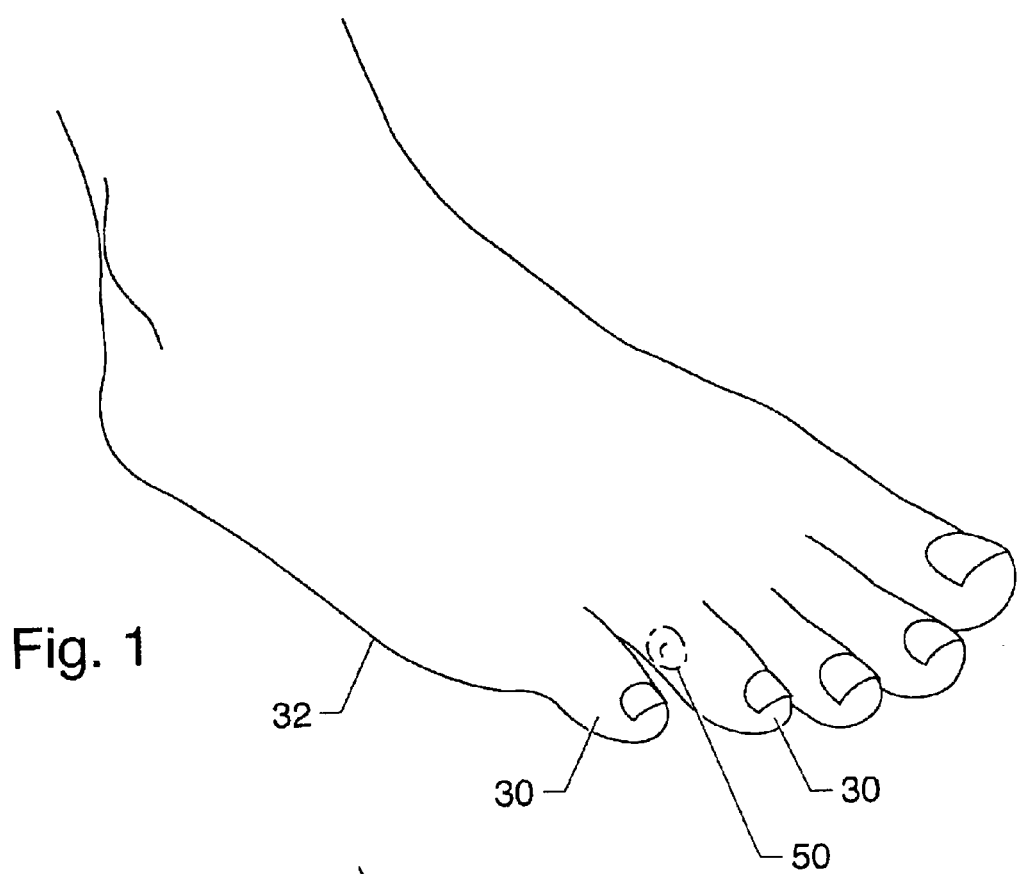
FIG. 1 is a perspective view of toes of the foot showing a soft corn (Heloma Molles).

There are two types of corns. The most common type develops on the tops and tips of the toes and along the sides of the feet. These are called heloma durums (hard corns) and are caused primarily by improper-fitting shoes and toe deformities. The second type develops between the toes, as shown in FIG. 1. These are called heloma molles (soft corns) and usually are the result of bone abnormalities in the toes. To eliminate the pain associated with soft corns it is necessary to eliminate the pressure point that causes the formation of the soft corn. The present invention is an alternative to other remedies such as pads and spacers and it is designed to reduce or eliminate the pressure points that still can remain with other solutions.

Figure 2:
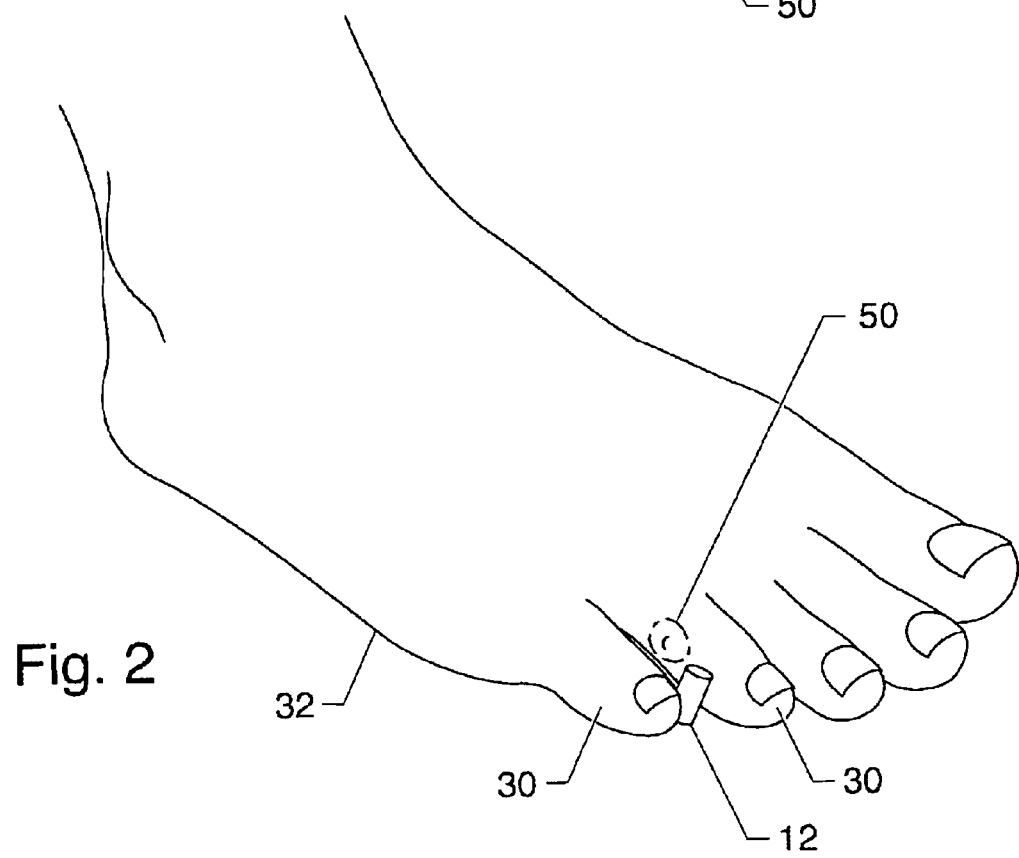
FIG. 2 is a perspective view of the foot and placement of a representative spacer of the present invention.
Figure 3:
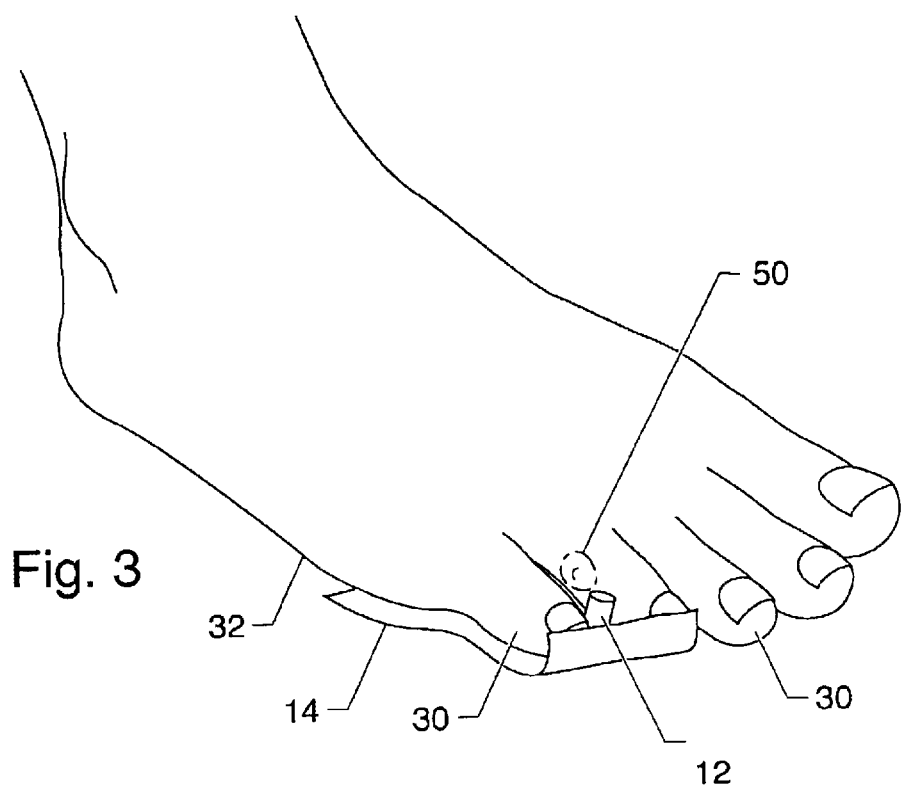
FIG. 3 is a perspective view of the foot with the spacer of FIG. 2 and placement of a representative mold dam of the present invention.
Figure 4:
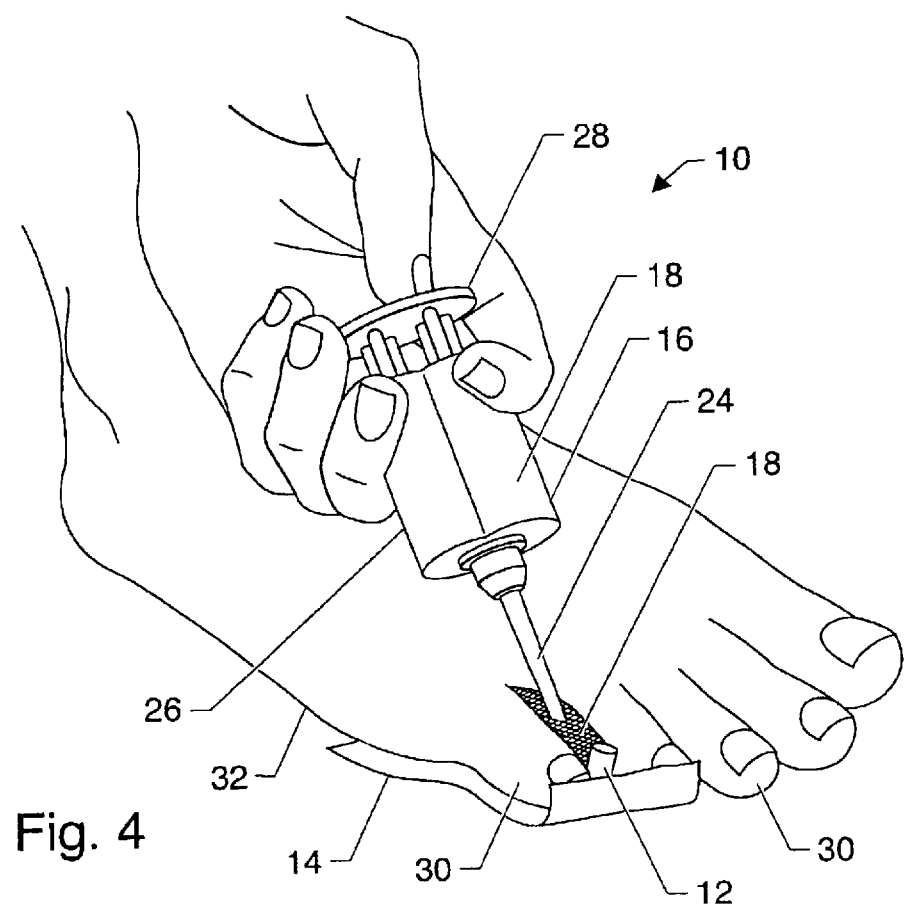
FIG. 4 is a perspective view of the foot with the spacer and mold dam of FIG. 3 and a representative application of the mold material using the mold applicator of the present invention.

Referring generally to FIGS. 2–4, one embodiment of the invention 10 comprises a spacer 12, a mold dam 14, a mold applicator 16 and mold material 18. As disclosed in more detail below, the spacer 12 is used to slightly separate the toes 30 from each other and the dam 14 is used to create a bottom wall onto which the mold material may be placed and to prevent the mold material 18 from escaping. Mold material 18 is injected between the toes, thus covering the corn 50, and allowed to cure, resulting in a generally solid, but flexible molded device 40 to protect the corn 50.

Referring now to FIGS. 2–4, the method for creating the molded device 40 is shown in more detail. The spacer 12 is a small device that can take the form of many shapes and sizes so long as the spacer 12, when inserted between the tips of toes 30, separates the toes 30 somewhat and leaves a small space about the thickness of a dime between the closest point between the toes, namely, between the corn 50 and the neighboring toe 30. The spacer 12 is inserted between the tips of the adjoining affected toes. That is, the spacer 12 is inserted between the two toes 30 between which the corn is located. The spacer 12 can be made from materials such as paper, plastic, wood, polystyrene or any relatively strong, relatively stable, inexpensive material that is nonirritating to human skin. A closed or open cell foam cylinder or cone that can be cut to a desired shape is suitable. It is not necessary that the spacer be made of adhesive material, nor is it necessary that adhesive material be applied to the spacer before use. The adductor toe muscles will hold the spacer 12 in place between the toes 30 as shown in FIG. 2.

Referring now to FIG. 3, with the spacer 12 in place, the mold dam 14 is applied to the bottom of the toes 30 and the foot 32. The mold dam 14 preferably is a thin piece of material used to secure the mold material 18 between the toes 30 and ensure that the mold material 18 remains in the proper position while curing. The mold dam 14 can take the form of various shapes and sizes so long as it extends generally from the ball of the foot 32 to the top of the spacer 12 at the ends of the toes 30. The mold dam 14 is as thin as possible depending on the material. The mold dam 14 can be made from materials such as tape, plastic, elastic or any relatively strong, relatively thin, inexpensive material that preferably is generally non-irritating to the human skin. Often, the mold dam 14 is a thin rectangle or triangle of flexible plastic, much like a large adhesive bandage, having a releasable adhesive on one side to stick to the bottom of the user's foot.

In one embodiment, the mold dam 14 is applied adhesive pointing upwards starting first with the ball of the foot 32 and working towards the tips of the toes 30, stopping at the top of the spacer 12. The adhesive allows the mold dam 14 to stick to and remain releasably attached to the bottom of the foot 32. In this fashion, the spacer 12, inserted first between the toes 30, creates a generally triangular space between the toes 30 (leaving a small space between the corn 50 and the neighboring toe 30) bounded by the spacer 12 and the neighboring toes 30, and the mold dam 14 creates the floor of the generally triangular space.

As disclosed above, one side of the mold dam 14 can be adhesive to hold the mold dam 14 to the bottom of the toes 30 and foot 32. Otherwise, the mold dam 14 can be held into place by the moisture and natural skin oils on the bottom of the toes 30 and foot 32. Although adhesive material is not necessary to hold the spacer 12 in place, additional adjustment of the spacer 12 may be required to get the proper width between toes 30. Both the mold dam 14 and the spacer 12 can be removed and reused after the mold material 18 has cured.

Referring now to FIG. 4, the tip 24 of the mold applicator 16 can be inserted between the toes 30 at the web 34 (the connection of the toes 30 to the foot 32) with the mold applicator 16 tilted toward the tips of the toes 30. The mold applicator tip 24 should be inserted as far forward as possible between the toes 30 without increasing the space between the toes 30 beyond that made by the spacer 12. The mold applicator tip 24 should touch or be proximal to the mold dam 14 to ensure that the mold material 18 adequately reaches the full sides of the toes 30 and fills in the now generally triangular three-dimensional space between the toes 30 and the spacer 30 and above the mold dam 14.

The mold applicator 16 can take the form of various shapes, structures and designs so long as it allows for the storage and injection of mold material 18 between the toes 30. For example, an illustrative mold application 16 can comprise a mold material receptacle 26, an applicator tip 24 and a dispensing mechanism 28. The mold applicator 16 can vary in size, depending on the size of its individual components. The mold applicator tip 24 can be up to or longer than 5 cm long, and preferably is in the range of 1–4 cm long. The mold applicator tip 24 can be between 2 mm wide or in diameter and up to approximately 1.3 cm wide or in diameter. The length and width of mold applicator tip 24 is not important except to allow the injection of a suitable quantity of mold material 18 between the toes 30 without causing extraneous separation of the toes 30. For example, in one embodiment, the mold applicator is a plastic syringe having one mold material receptacle 26 for a single-component mold material 18 or with two parallel mold material receptacles 26 for a double-component mold material 18. In another example, in another embodiment, the mold applicator 16 can be a plastic bag with an applicator tip affixed to the bottom of the bag.

Figure 5:
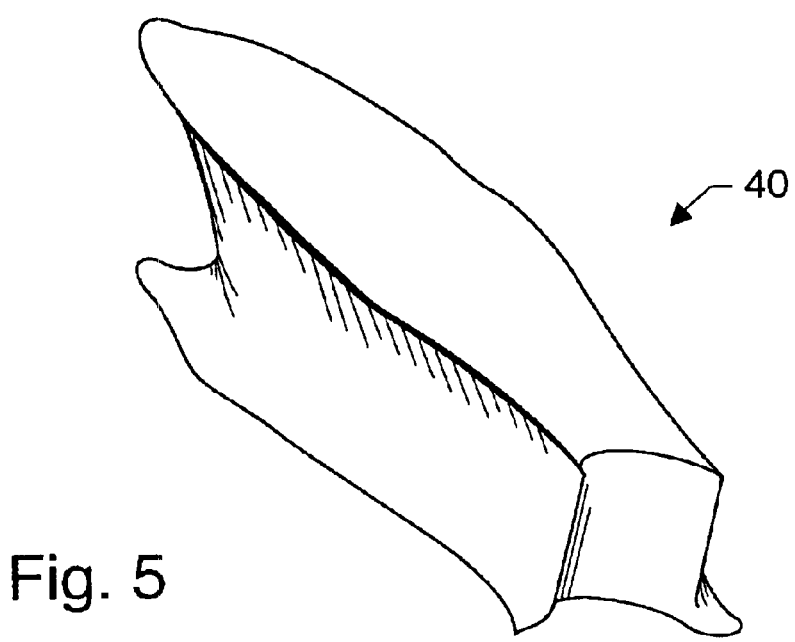
FIG. 5 is a perspective view of a representative formed mold after completion.
Figure 5A:
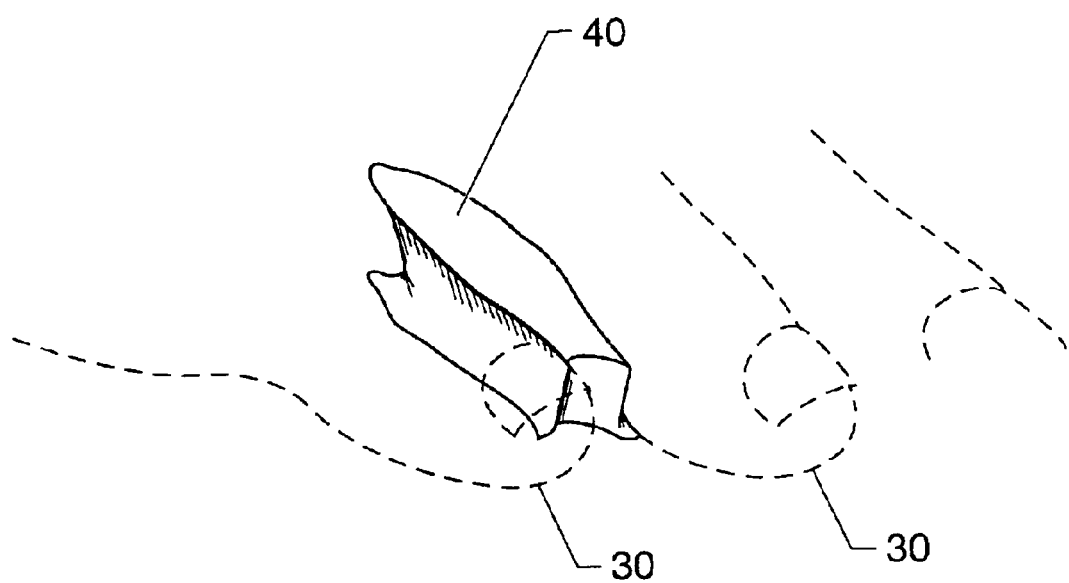
FIG. 5A is a perspective view of the completed formed mold of FIG. 5 in relation to the toes.

As shown in more detail in FIG. 4, the mold applicator 16 is operated by dispensing the mold material 18 to fill the gap between the toes 30. Specifically, the mold applicator tip 24 is inserted between the toes 30, and dispensing mechanism 28, such as the plunger or plungers shown in FIG. 4, is activated, forcing the mold material 18 out of the mold applicator 16 and into the space between the toes 30. As the mold material 18 is applied in this embodiment, the mold applicator 16 is lifted generally upwards and rearwards as the mold material 18 fills the space between the toes 30. To finish the mold 40, as shown in FIGS. 5 and 5A, the top layer of mold material 18 can be applied with a forward motion towards the tips of the toes 30. The mold material 18 can completely cover the space between the toes 30 all the way to the top of the toes 30. The mold material 18 can be applied in an amount sufficient to fill the space between the toes 30 to prevent, when cured, the corn 50 from touching or being forced against the neighboring toe 30. Too much mold material 18 should not be applied as this will force the toes 30 apart.

The preferred mold material 18 is a soft, flexible and sculptable substance having the ability to conform to an object in fine detail, release little heat upon curing, and set easily without contracting as it cures. The mold material 18 preferably hardens quickly and is non-irritating and non-toxic to human skin. For illustrative purposes, a preferred mold material 18 will take less than two minutes to insert between the toes, will begin to cure In approximately two minutes, and will completely cure in fifteen minutes or less. When dry, the mold material 18 preferably is oblivious or highly resistant to any chemicals approved for contact with the skin, allowing the use of medications while using the mold 40 and the cleaning of the mold 40 when necessary. Also when dry, the mold material 18 preferably is very durable, will maintain its unique shape and will retain its elasticity and comfort. The flexibility of the final mold 40 helps to insure that the mold 40 will stay in place during physical activity.

Although any known or future developed mold material 18 satisfying the criteria disclosed above is suitable, some illustrative mold materials 18 include the category of dental molding materials. For example, the mold material 18 can be a two-component material that when mixed together hardens into a rubbery material. In one embodiment, the mold material 18 can be a dental grade vinyl polysiloxane, a mixture of polydimethyl vinyl siloxane, polydimethyl hydrogen siloxane, silica and paraffine. Vinyl polysiloxane, often referred to as VPS, is widely used as a dental impression material to form bridges and crowns. VPS is non-toxic to skin and a minor irritant to eyes. In the present invention, VPS will be for external use only.

After injecting the mold material 18 between the toes 10, when the top of the mold material 18 feels solid to the touch, the mold material 18 has set. Once the mold material 18 has set, the mold dam 14 and spacer 12 can be removed. The toes 30 can be gently pulled apart and away from the molded device 40. The molded device 40 can be removed and trimmed of any external flashing using a sharp knife, razor blade or scissors. Care should be taken to not cut or trim the sides where the molded device 40 comes in contact between the toes 30.

Referring now to FIGS. 5 and 5A, the present invention 10 insures exacting, high definition conformity to the user's physical toe and corn conformation. The molded device 40 is an exact copy of the space between the users toes 30, and if prepared properly, forms a soft and flexible covering for the corn 50 that allows the pressure of a neighboring toe 30 or sock or shoe to be more evenly distributed about the corn 50, onto the healthy tissue of the toes 30, and/or away from the corn 50. The molded device 40 can be removed for showering and cleaning, and reused. In addition, the molded device 40 requires no straps or bands to hold it in place and its unique "I beam" shape and flexibility insures that it will stay in place during physical activity.

Figure 6:
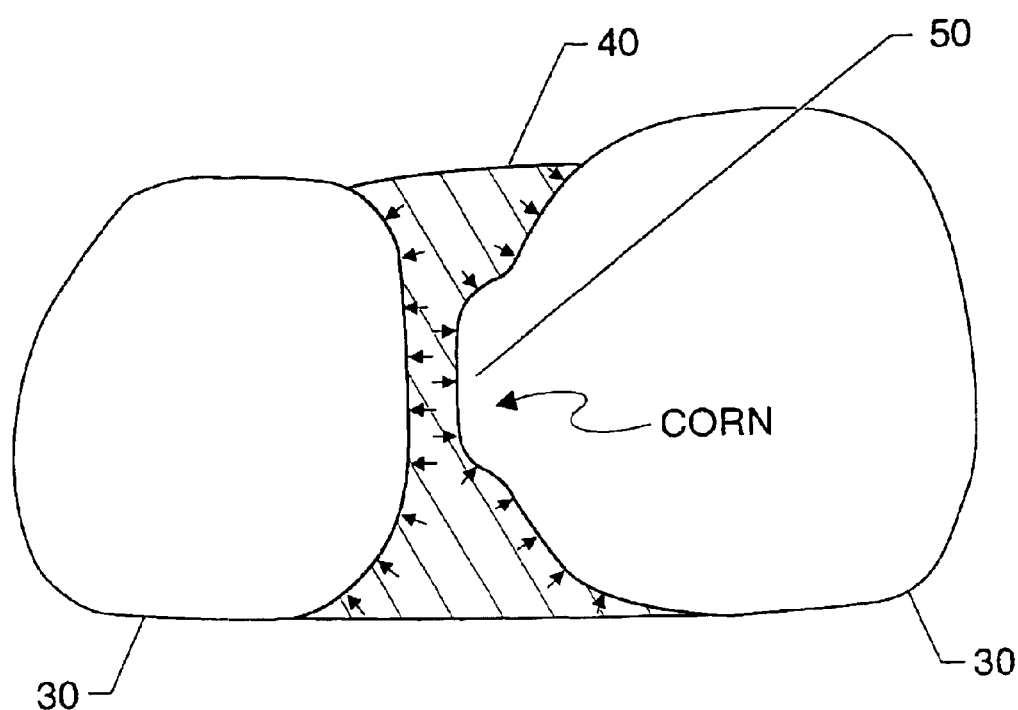
FIG. 6 is a cross-sectional view of toes showing the unique shape of the formed device and illustrating the even distribution of pressure throughout the mold.
Figure 6A:
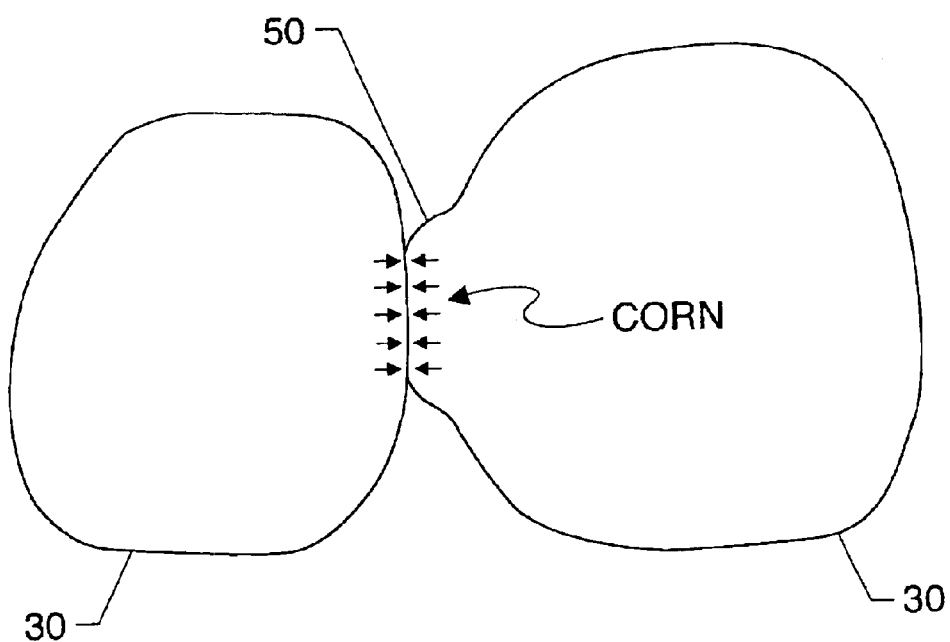
FIG. 6A is a cross-sectional view of toes without the device showing concentration of pressure points on the corn.

Referring now to FIGS. 6 and 6A, the use of a completed molded device 40 is shown in comparison to not using a completed molded device 40. As shown in FIG. 6, the molded device 40 conforms to the shape of the corn 50 in a manner which distributes externally-applied pressure throughout the molded device 40, thus alleviating pressure on the corn 50 and reducing pain. To eliminate the pain associated with soft corns it is necessary to eliminate the pressure point that causes the formation of the soft corn, as shown in FIG. 6A. By molding the molded device 40 in place, the present invention 10 eliminates or greatly reduces the pressure point on a corn 50 by transferring all or most of the pressure evenly between the toes 30. Further, because pressure is distributed evenly and the molded device 40 is custom fit to the user, the molded device 40 does not irritate healthy tissue surrounding the corn 50 and the adjacent toes 30. Moreover, the molded device 40 demonstrates high durability in extremely thin cross-sections allowing for minimal width to achieve even pressure distribution while ensuring comfort. If, after a week or two of using the molded device 40, the corn 50 starts to go away, a new molded device 40 can be made for the new-shaped corn 50. This will prevent the occurrence of new pressure points resulting in the formation of new corns 50.

The above detailed description of the preferred embodiments and the appended figures are for illustrative purposes only and are not intended b limit the scope and spirit of the invention, and its equivalents, as defined by the appended claims. One skilled in the art will recognize that many variations can be made to the invention disclosed in this specification without departing from the scope and spirit of the invention.

What is claimed is:

1. A method for the symptomatic relief or pain caused by a corn on the human toe, comprising the steps of:
   a. inserting a spacer between a toe having a corn and a neighboring toe so as to create a space between the toe having the corn and the neighboring toe;
   b. injecting a moldable and curable molding material in the space between the toe having the corn and the neighboring toe and allowing the molding material to cure to form a molded device; and
   c. leaving the molded device in place between the toe having the corn and the neighboring toe whereby the molded device protects the corn by in part transferring pressure around the corn to neighboring healthy tissue.

2. The method as claimed in claim 1, wherein the spacer is inserted between the toe having the corn and the neighboring toe a sufficient distance to separate the toe having the corn from the neighboring toe such that the corn does not touch the neighboring toe.

3. The method as claimed in claim 2, wherein the space between the toe having the corn and the neighboring toe is completely filled with the molding material.

4. The method as claimed in claim 3, wherein the molding material initially is a viscous material that cures into a visco-elastic material.

5. The method as claimed in claim 4, wherein the molded device can be removed from between the toe having the corn and the neighboring toe for trimming and cleaning.

6. The method as claimed in claim 3, wherein the molding material is non-toxic and non-irritating to human skin.

7. The method as claimed in claim 1, further comprising the steps of removing the spacer after the molding material has cured.

8. A method for the symptomatic relief or pain caused by a corn on the human toe, comprising the steps of:
   a. inserting a spacer between a toe having a corn and a neighboring toe so as to create a space between the toe having the corn and the neighboring toe;
   b. providing a dam underneath the toe having the corn and the neighboring toe, which dam extends from proximal to where the toe having the corn and the neighboring toe connect to a foot, underneath the toe having the corn and the neighboring toe and the space therebetween, and upwards about the tips of the toe having the corn and the neighboring toe, thereby creating a three-dimensional volume between the toe having the corn and the neighboring toe bounded by the dam, the toe having the corn and the neighboring toe;
   c. injecting a moldable and curable molding material in the space between the toe having the corn and the neighboring toe and allowing the molding material to cure to form a molded device; and
   d. leaving the molded device in place between the toe having the corn and the neighboring toe whereby the molded device protects the corn by in part transferring pressure around the corn to neighboring healthy tissue.

9. The method as claimed in claim 8, wherein the spacer is inserted between the toe having the corn and the neighboring toe a sufficient distance to separate the toe having the corn from the neighboring toe such that the corn does not touch the neighboring toe.

10. The method as claimed in claim 9, wherein the space between the toe having the corn and the neighboring toe is completely filled with the molding material.

11. The method as claimed in claim 10, wherein the molding material initially is a viscous material that cures into a visco-elastic material.

12. The method as claimed in claim 11, wherein the molded device can be removed from between the toe having the corn and the neighboring toe for trimming and cleaning.

13. The method as claimed in claim 10, wherein the molding material is non-toxic and non-irritating to human skin.

14. The method as claimed in claim 8, further comprising the steps of removing the spacer and the dam after the molding material has cured.

15. A system for the symptomatic relief or pain caused by a corn on the human toe, comprising:
   a. providing means for creating a molded device between a toe having a corn and a neighboring toe;
   b. creating the molded device as a custom-made and shaped component for protecting the corn; and
   c. inserting the molded device between the toe having the corn and the neighboring toe so as to cover the corn, whereby the molded device protects the corn by in part transferring pressure around the corn to neighboring healthy tissue,
   wherein the molded device is created by a method comprising the steps of:
   i. inserting a spacer between the toe having a corn and the neighboring toe so as to create a space between the toe having the corn and the neighboring toe; and
   ii. injecting a moldable and curable molding material in the space between the toe having the corn and the neighboring toe and allowing the molding material to cure to form the molded device.

16. The system as claimed in claim 15, wherein the spacer is inserted between the toe having the corn and the neighboring toe a sufficient distance to separate the toe having the corn from the neighboring toe such that the corn does not touch the neighboring toe.

17. The system as claimed in claim 16, wherein the space between the toe having the corn and the neighboring toe is completely filled with the molding material.

18. The system as claimed in claim 17, wherein the molded device can be removed from between the toe having the corn and the neighboring toe for trimming and cleaning.

19. The system as claimed in claim 18, wherein the molding material is non-toxic and non-irritating to human skin.

20. The system as claimed in claim 19, further comprising the steps of removing the spacer after the molding material has cured.

21. A system for the symptomatic relief or pain caused by a corn on the human toe, comprising:
   a. providing means for creating a molded device between a toe having a corn and a neighboring toe;
   b. creating the molded device as a custom-made and shaped component for protecting the corn; and
   c. inserting the molded device between the toe having the corn and the neighboring toe so as to cover the corn, whereby the molded device protects the corn by in part transferring pressure around the corn to neighboring healthy tissue,
   wherein the molded device is created by a method comprising the steps of:
   i. inserting a spacer between the toe having a corn and the neighboring toe so as to create a space between the toe having the corn and the neighboring toe;
   ii. providing a dam underneath the toe having the corn and the neighboring toe, which dam extends from proximal to where the toe having the corn and the neighboring toe connect to a foot, underneath the toe having the corn and the neighboring toe and the space therebetween, and upwards about the tips of the toe having the corn and the neighboring toe, thereby creating a three-dimensional volume between the toe having the corn and the neighboring toe bounded by the dam, the toe having the corn and the neighboring toe; and
   iii. injecting a moldable and curable molding material in the space between the toe having the corn and the neighboring toe and allowing the molding material to cure to form the molded device.

22. The system as claimed in claim 21, wherein the spacer is inserted between the toe having the corn and the neighboring toe a sufficient distance to separate the toe having the corn from the neighboring toe such that the corn does not touch the neighboring toe.

23. The system as claimed in claim 22, wherein the space between the toe having the corn and the neighboring toe is completely filled with the molding material.

24. The system as claimed in claim 23, wherein the molded device can be removed from between the toe having the corn and the neighboring toe for trimming and cleaning.

25. The system as claimed in claim 24, wherein the molding material is non-toxic and non-irritating to human skin.

26. The system as claimed in claim 25, further comprising the steps of removing the spacer after the molding material has cured.

27. A device for the symptomatic relief or pain caused by a corn on the human toe comprising a molded in place component for placement in the space between a toe having a corn and a neighboring toe, wherein the molded in place component is comprised of a molding material that initially is a viscous material and that cures into a visco-elastic material and is created by a method comprising the steps of:
   a. inserting a spacer between the toe having a corn and the neighboring toe so as to create a space between the toe having the corn and the neighboring toe; and
   b. injecting the molding material in the space between the toe having the corn and the neighboring toe and allowing the molding material to cure to form the molded device.

28. The device as claimed in claim 27, wherein the spacer is inserted between the toe having the corn and the neighboring toe a sufficient distance to separate the toe having the corn from the neighboring toe such that the corn does not touch the neighboring toe.

29. The device as claimed in claim 28, wherein molded in place component completely fills the space between the toe having the corn and the neighboring toe.

30. The device as claimed in claim 29, wherein the molded in place component is removable from between the toe having the corn and the neighboring toe.

31. The device as claimed in claim 30, wherein the molded in place component is non-toxic and non-irritating to human skin.

32. A device for the symptomatic relief or pain caused by a corn on the human toe comprising a molded in place component for placement in the space between a toe having a corn and a neighboring toe, wherein the molded in place component is comprised of a molding material that initially is a viscous material and that cures into a visco-elastic material and is created by a method comprising the steps of:
   a. inserting a spacer between the toe having a corn and the neighboring toe so as to create a space between the toe having the corn and the neighboring toe;
   b. providing a dam underneath the toe having the corn and the neighboring toe, which dam extends from proximal to where the toe having the corn and the neighboring toe connect to a foot, underneath the toe having the corn and the neighboring toe and the space therebetween, and upwards about the tips of the toe having the corn and the neighboring toe, thereby creating a three-dimensional volume between the toe having the corn and the neighboring toe bounded by the dam, the toe having the corn and the neighboring toe; and
   c. injecting the molding material in the space between the toe having the corn and the neighboring toe and allowing the molding material to cure to form a molded device.

33. The device as claimed in claim 32, wherein the spacer is inserted between the toe having the corn and the neighboring toe a sufficient distance to separate the toe having the corn from the neighboring toe such that the corn does not touch the neighboring toe.

34. The device as claimed in claim 33, wherein the molding material completely fills the space between the toe having the corn and the neighboring toe.

35. The device as claimed in claim 34, wherein the molded in place component is removable from between the toe having the corn and the neighboring toe.

36. The device as claimed in claim 35, wherein the molding material is non-toxic and non-irritating to human skin.

37. The device as claimed in claim 36, wherein the molding material is a vinyl polysiloxane.

* * * * *